United States Patent [19]

Fayngold et al.

[11] Patent Number: 5,328,473
[45] Date of Patent: Jul. 12, 1994

[54] DISPOSABLE NEEDLE HOLDER

[75] Inventors: Zev Fayngold, Livingston; Sam Zhadanov, Metuchen, both of N.J.

[73] Assignee: Becton, Dickinson and Company, Franklin Lakes, N.J.

[21] Appl. No.: 54,570

[22] Filed: Apr. 28, 1993

[51] Int. Cl.⁵ .............................................. A61M 5/00
[52] U.S. Cl. .................... 604/110; 604/198; 604/263
[58] Field of Search ............. 604/110, 187, 192, 195, 604/198, 263; 126/763, 764, 765

[56] References Cited

U.S. PATENT DOCUMENTS

| | | | |
|---|---|---|---|
| 4,790,827 | 12/1988 | Haber et al. | 128/763 X |
| 4,840,185 | 6/1989 | Hernandez | 128/763 |
| 4,871,355 | 10/1989 | Kikkawa | 604/198 |
| 4,915,702 | 4/1990 | Haber | 604/198 |
| 4,984,580 | 1/1991 | Wanamaker | 128/763 |

Primary Examiner—John D. Yasko
Attorney, Agent, or Firm—Alan W. Fiedler

[57] ABSTRACT

A needle holder assembly having a sleeve that slidably receives a needle holder having a needle assembly attached thereto. After the need holder assembly has been used to collect a sample of body fluid, the needle holder is slid from its initial retracted position to a permanently locked extended position. In the extended position the used needle is contained within the sleeve of the assembly and can be disposed of. The assembly of the present invention includes a mechanism for smoothly releasing the needle holder from the retracted position, an improved mechanism for permanently and securely locking the needle holder in the extended position, and a body fluid collection channel around the distal end of the sleeve that prevents body fluid from splattering from the distal end of the assembly, when the sleeve is locked in the needle holder.

16 Claims, 5 Drawing Sheets

DISPOSABLE NEEDLE HOLDER

BACKGROUND OF THE INVENTION

1. Field of the Invention

The present invention relates to an improved needle holder assembly and, more particularly, a needle holder assembly having a release mechanism for smoothly releasing the needle holder from a retracted position to permit the needle holder to slide within a sleeve to an extended position at which the holder is permanently locked for disposal by an improved locking mechanism.

2. Background Description

A needle holder assembly is commonly used in hospitals and doctors offices to aid in drawing body fluid, e.g., blood, from a patient for diagnostic testing and other procedures. Needle holder assemblies primarily consist of a hollow cylinder inner tube body or needle holder that holds a standard double-ended hollow needle at its distal end with one end of the needle extending into the tube and the other end extending out of the tube for piercing the patient's skin extending. The tube body is shaped to receive an evacuated collection tube having a piercable closure so that the closure is pierced by the internal end of the needle and body fluid is drawn by the vacuum from the patient into the collection tube. An example of a piercable closure that is currently being used to seal evacuated tubes is the HEMOGARD TM Closure for use on the VACUTAINER Brand tube from Becton, Dickinson and Company. The HEMOGARD TM Closure is basically a rubber stopper covered by a plastic shield, however, a more detailed description of the closure is contained in U.S. Pat. Nos. 4,741,446 (Miller) and 4,991,104 (Miller), both of which are assigned to Becton, Dickinson and Company and incorporated herein by reference.

Needle holder assemblies have also been made having an outer safety shield or sleeve that slidably receives the hollow cylinder inner tube, described above, the sleeve being slightly larger in diameter than the inner tube which permits the inner tube to slide within the sleeve from a retracted position to an extended position. When the inner tube is in the retracted position, the needle extends out of an opening in the distal end of the sleeve and when the inner tube is in the extended position, the needle is contained within and surrounded by the sleeve so that the needle holder assembly can be disposed of. Such needle holder assemblies are very useful and valuable since they minimize the chance of accidental needle sticks occurring after the assembly has been disposed of by surrounding the sharp point of the used needle.

A needle holder assembly of the type described above is shown in U.S. Pat. No. 4,923,445 (Ryan). The Ryan assembly includes a hollow cylindrical inner tube body with a needle at its forward end and an outer shield arranged to slidably receive the inner tube body. The inner tube slides from a retracted position to an extended position and includes a locking mechanism to lock the shield in the extended position. The locking mechanism, however, does not permanently and securely lock the inner tube and sleeve together, since it merely retains the inner tube in the retracted position by using solid protrusions on the wall of the shield to engage a groove on the inner tube. However, the protrusions can easily be disengaged from the groove using moderate force and some wiggle. Therefore, the Ryan assembly does not provide the secure permanent locking action that is required to safely dispose of a used holder, since the holder could be pushed easily towards the retracted position and expose the needle beyond the shield. Another disadvantage of the Ryan assembly is that it is difficult to disengage from the retracted position, since rotation of the inner tube is prevented by a ratchet mechanism that locks the inner tube and shield together when the assembly is in the retracted position.

U.S. Pat. No. 4,947,863 (Haber et al.) and Re. 33,585 (Haber et al.) also describe collection tube holders like those discussed above. The Haber et al. holders also include a shock absorbing system with deceleration stations that absorb and dampen vibrations that are generated by the jarring impact forces when the outer sleeve is advanced and locked in the extended position. However, the Haber et al. holders do not address the need for permanently and securely locking the inner tube to the sleeve at the extended position or providing a release mechanism for smoothly releasing the inner tube from the retracted position.

SUMMARY OF THE INVENTION

The present invention overcomes the problems identified in the background material by providing a needle holder assembly having an needle holder and a sleeve with a number of special features. For example, a preferred needle holder assembly according to the present invention includes a locking mechanism that permanently and securely locks the needle holder to the sleeve at the extended position and a release mechanism that smoothly releases the needle holder from the retracted position.

A preferred locking mechanism according to the present invention includes a plurality of angled freestanding flexible fingers that extend from an interior wall of the sleeve and lock in a groove around the distal end of the needle holder, when the needle holder is in the extended position. The flexible fingers expand in the groove when the needle holder is moved and thereby provide the beneficial feature of permanently and securely mating and locking with the groove to prevent any axial movement of the holder in the sleeve.

The needle holder assembly of the present invention also includes a preferred release mechanism comprising a plurality of lead threads on the inner wall at the distal end of the sleeve. The lead threads cause the needle holder to slowly back out of the sleeve from the retracted position towards the extended position as the needle holder is rotated, which smoothly releases the needle holder from the retracted position and reduces the possibility of body fluid splatter that may occur if the release action is too abrupt.

Finally, the needle holder assembly of the present invention includes an annular channel around the opening at the distal end of the sleeve, which prevents any body fluid from splattering from the distal end of the sleeve when the needle holder has been locked in the extended position within the sleeve. The prevention of accidental splattering from the distal end of the assembly is also important when used assemblies are being transported and disposed of.

These and other aspects, features and advantages of the present invention will become apparent from the following detailed description taken in conjunction with the accompanying drawings.

DETAILED DESCRIPTION

Figure 1A:
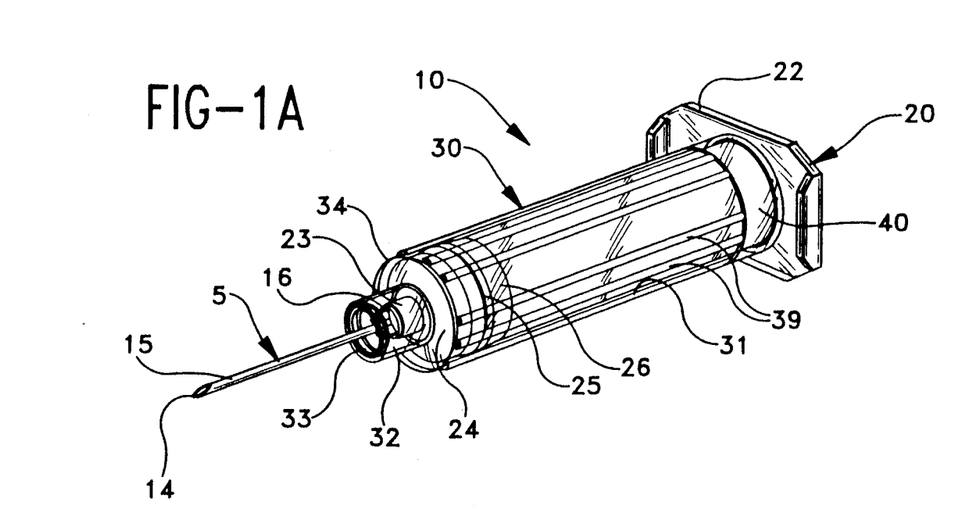
FIG. 1A is a perspective view of a preferred needle holder assembly of the present invention in a retracted position.
Figure 1B:
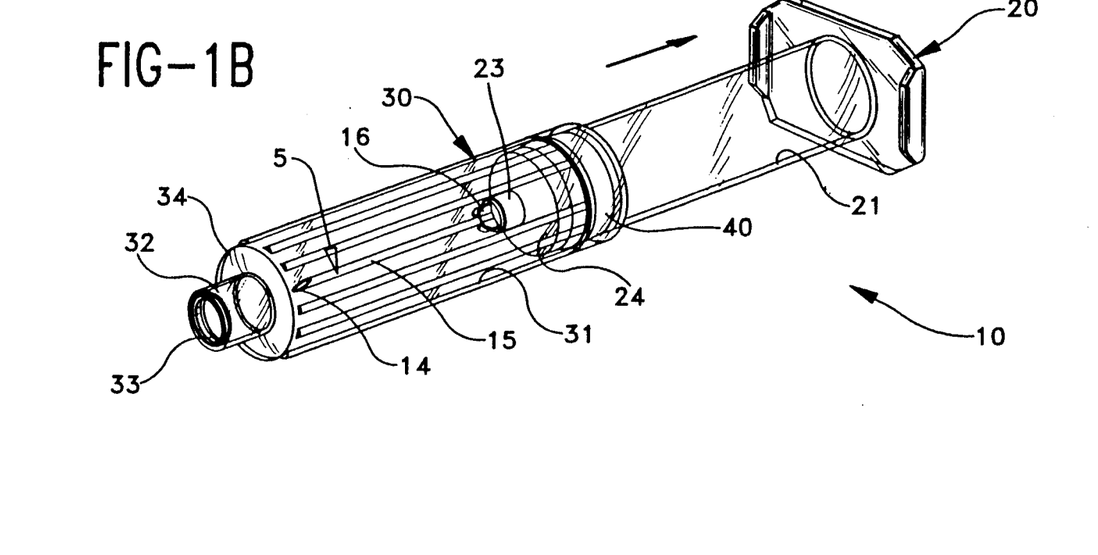
Fig. 1B is a perspective view of the needle holder assembly shown in FIG. 1A in an extended position.

FIGS. 1A and 1B are perspective views of a preferred needle holder assembly 10 of the present invention. FIG. 1A shows assembly 10 in a retracted position and FIG. 1B shows assembly 10 in a permanently locked extended position.

Needle holder assembly 10 shown in FIGS. 1A and 1B generally includes a needle assembly 5, a needle holder 20, and an outer sleeve 30. Needle holder 20 is slidably received within a proximal open end 40 of outer sleeve 30. In used in the retracted position shown in FIG. 1A to draw a sample or more of body fluid from a patient and then is slid from the retracted position to the extended position shown in Fig. 1B. When needle holder 20 is finally slid to the extended position, it is permanently and securely locked to outer sleeve 30 by a locking mechanism, described below, and cannot be moved to any other position. Therefore, when assembly 10 is in the extended position it can be disposed of.

Needle holder 20 includes a cylinder wall 21 having a flange 22 with a pair of tabs 28 at its proximal end and a shoulder 24 at its distal end tapering to a threaded neck 23. Neck 23 has threads that mate with a matching thread 12 on a base 11 of needle assembly 5 to securely hold needle assembly 5 in holder 20. Needle holder 20 also includes a pair of ramps 25 and 27 with a groove 26 positioned therebetween which are shown in more detail in FIGS. 2 and 3, described below.

Outer sleeve 30 includes a wall 31 extending axially from a distal end to a proximal end with a plurality of ribs 39 extending longitudinally on an outer surface of wall 31. A shoulder 34 at the distal end of outer wall 31 tapers to an annular cylindrical neck 32 having an annular toroid-shaped channel 33 at the distal open end of sleeve 30. Cannula 15 of needle assembly 5 includes a distal needle point 14 that extends beyond neck 32 and channel 33, when needle holder 20 is in the retracted position shown in FIG. 1A, so that point 14 is ready to pierce a patient to draw a sample of body fluid.

Figure 2:
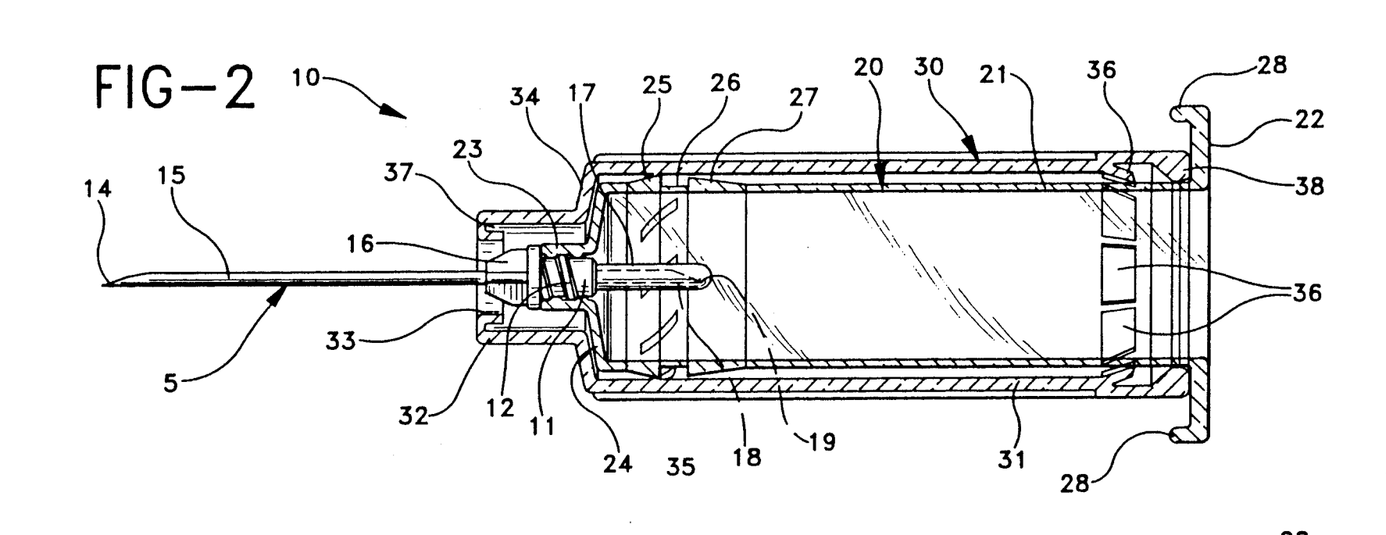
FIG. 2 is a cross-sectional view of the needle holder assembly shown in FIG. 1A.

FIG. 2 is a cross-sectional view of needle holder assembly 10 shown in FIG. 1A, with needle holder 20 in the retracted position. As shown in FIG. 2, base 11 on needle hub 16 of needle assembly 5 is screwed into neck 23 of needle holder 20. In particular, thread 12 on base 11 of needle hub 16 mates with the thread in neck 23 to firmly attach needle assembly 5 to needle holder 20. When needle assembly 5 has been attached to needle holder 20, exterior cannula 15 extends out of neck 23 so that distal needle point 14 can be used to pierce a patient's skin. An interior cannula 18 on needle assembly 5 extends into needle holder 20 and includes a needle point 19 that is received in a flexible seal 17, which seals cannula 18 to prevent body fluid from flowing into needle holder 20. However, when an evacuated tube is mounted in needle holder 20, a closure on the tube is pierced by point 19 of cannula 18 and seal 17 is pushed down interior cannula 18 so to allow body fluid to flow through cannula 15 and cannula 18 into the tube in holder 20. When the tube has drawn the desired amount of body fluid it is removed, permitting seal 17 to again seal cannula 18. Additional tubes can then be inserted into holder 20 to draw additional body fluid samples.

As shown in FIG. 2, shoulder 24 of needle holder 20 abuts the interior surface of shoulder 34 on sleeve 30 when assembly 10 is in the retracted position. Contact between shoulder 24 and 34 prevents holder 20 from advancing any further in the distal direction. To prevent holder 20 from sliding in the proximal direction, a plurality of lead threads 35 on sleeve 30 mate with ramp 25 on the outer surface of cylinder wall 21 on holder 20. The interaction between lead threads 35 and ramp 25, retain holder 20 in the retracted position and prevent it from unintentionally sliding out of position. Maintaining holder 20 in the retracted position within sleeve 30 is particularly important when needle assembly 5 is being screwed into holder 20 and assembly 10 is being transported prior to use.

Figure 3:
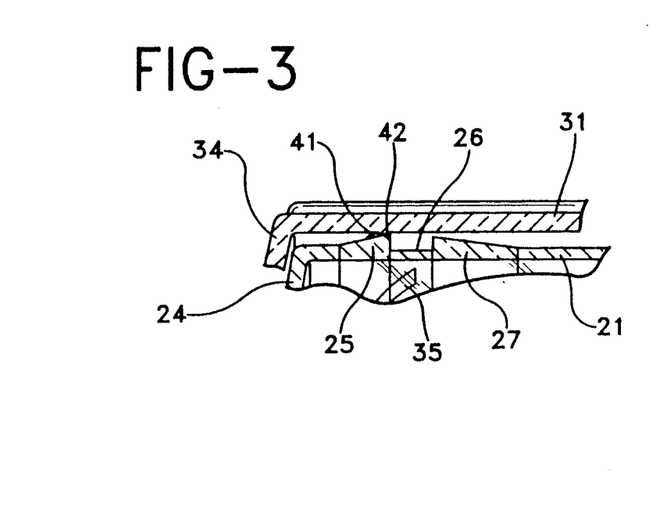
FIG. 3 is an enlarged cross-sectional view of a portion of FIG. 2.

The plurality of lead threads 35 and ramp 25 also combine to provide a release mechanism for assembly 10 that smoothly releases needle holder 20 from the retracted position, when holder 20 is rotated in a counterclockwise direction. Interaction between threads 35 and ramp 25, when assembly 10 is in the retracted position, is more clearly shown in FIG. 3 which is an enlarged cross-sectional view of a portion of FIG. 2. More particularly, FIG. 3 shows an upper edge portion 41 on thread 35 in sleeve 30 biting into an edge portion 42 of ramp 25 on holder 20. After assembly 10 has been used to draw body fluid from a patient and cannula 15 has been withdrawn from the patient's arm, holder 20 is rotated in a counterclockwise direction while firmly holding sleeve 30 in place. The counterclockwise rotation of holder 20 causes threads 35 of the release mechanism to slowly and smoothly back holder 20 out of sleeve 30 from the retracted position. A benefit resulting from smoothly releasing holder 20 from the retracted position in sleeve 30 is the prevention of inadvertent splatter of body fluid that may remain on the end of cannula 15 in needle assembly 5. After the release mechanism has been used to release holder 20 from the retracted position, holder 20 can be easily slide to the extended position within sleeve 30 where holder 20 is locked in place by a locking mechanism and disposed of.

Figure 4:
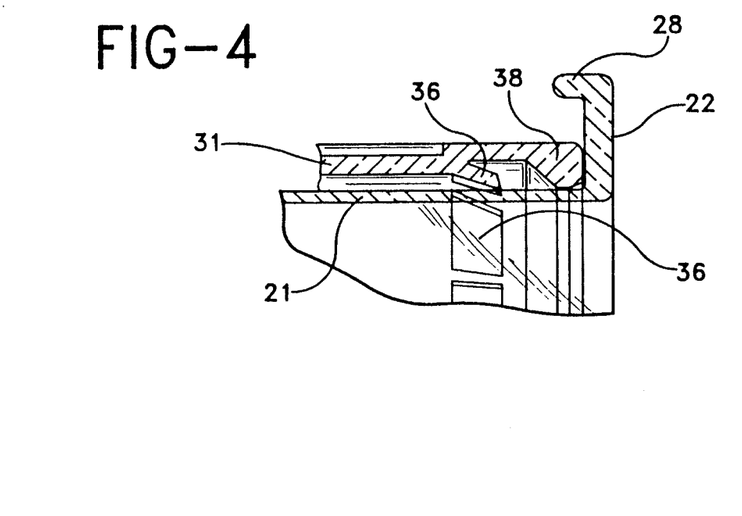
FIG. 4 is an enlarged cross-sectional view of a portion of FIG. 2.

FIG. 2 also shows a segmented annular projection 36 at the proximal end of wall 31 comprising a plurality of free-standing flexible fingers or segments. Each segment of projection 36 is attached to wall 31 on one end, with the other end of each segment of projection 36 extending away from wall 31 into sleeve 30 to contact wall 21, as shown in detail in FIG. 4. In addition, an annular support 38 is provided at the proximal end of sleeve 30 that projects into sleeve 30 and also makes contact with wall 21 of needle holder 20. Both of these features provide support for holder 20 within sleeve 30 near the proximal end of assembly 10 to maintain the relative alignment between holder 20 and sleeve 30. FIG. 4 is an enlarged cross-sectional view of the proximal end portion of assembly 10, shown in FIG. 2, and more clearly shows the interaction between projection 36, annular support 38 and wall 21.

Figure 5:
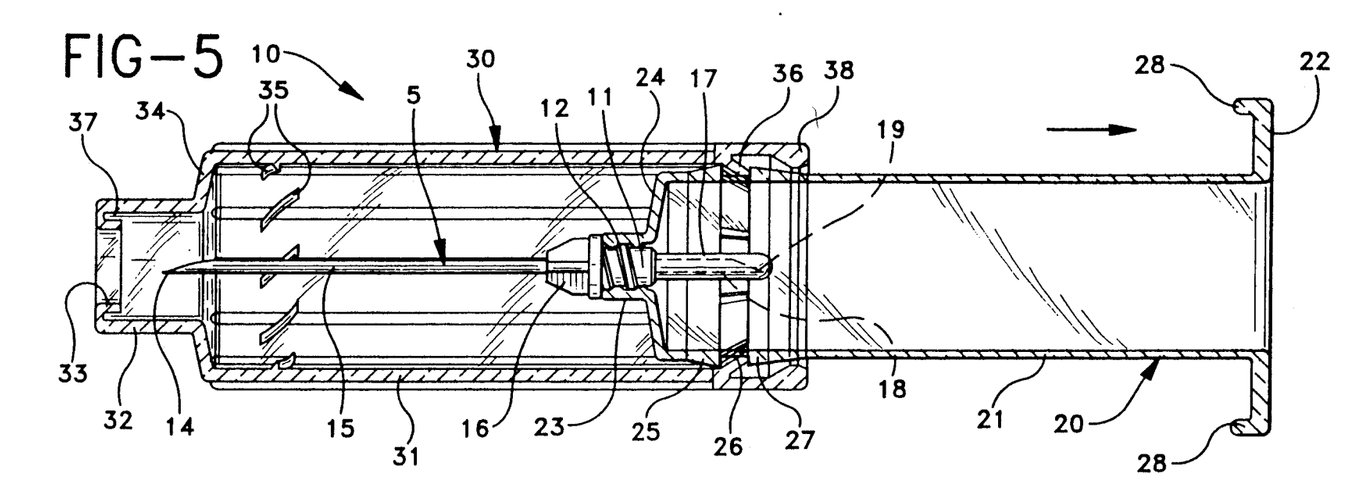
FIG. 5 is a cross-sectional view of the needle holder assembly shown in FIG. 1B.
Figure 6:
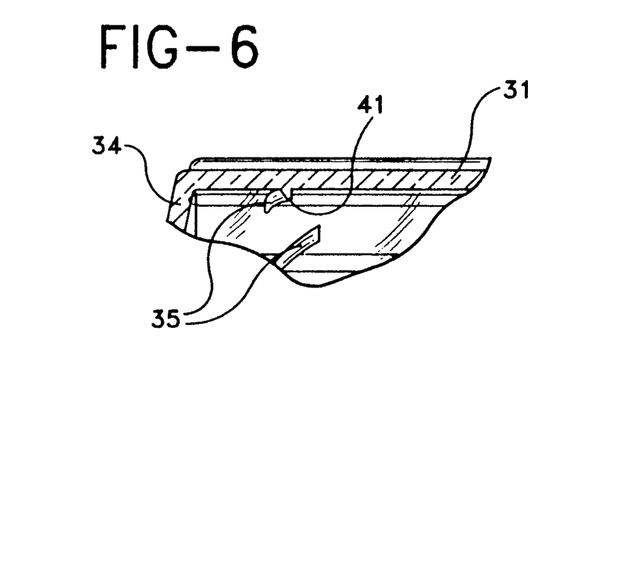
FIG. 6 is an enlarged cross-sectional view of a portion of FIG. 5.
Figure 7:
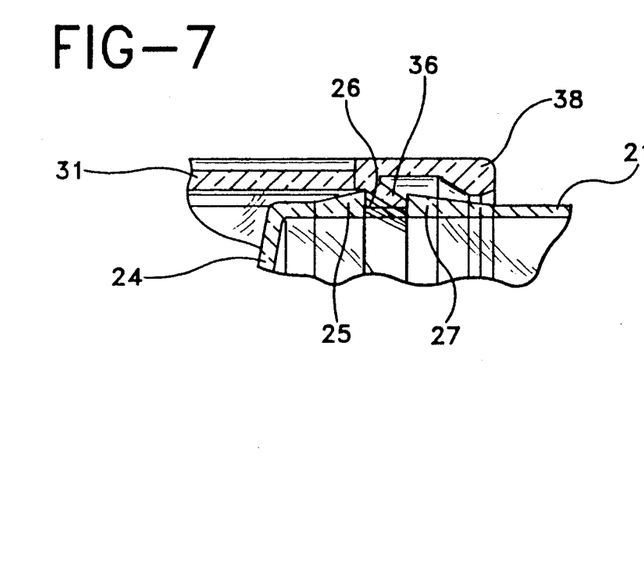
FIG. 7 is an enlarged cross-sectional view of a portion of FIG. 5.

FIGS. 5, 6 and 7 are cross-sectional views of needle holder assembly 10 in the extended position, as shown in Fig. 1B. In particular, FIG. 5 shows holder 20 after it has slid within sleeve 30 from the retracted position to the extended position. As holder 20 is slid within sleeve 30 segmented annular projection 36 and annular support 38 slide on the exterior surface of cylinder wall 21 in holder 20 and cooperate to firmly stabilize holder 20 within sleeve 30. In addition, after holder 20 has substantially moved from the retracted position, upper edge 41 on each lead thread 35 on the interior surface of wall 31 in sleeve 30 are no longer in contact with holder 20, as shown in FIG. 6.

When holder 20 arrives at the extended position within sleeve 30, segmented projection 36 slides up ramp 27 and snaps into groove 26. After projection 36 has snapped into groove 26, holder 20 is permanently and securely locked in the extended position by a locking mechanism comprising segmented annular projection 36, ramps 25 and 27, and groove 26. The locking mechanism prevents holder 20 from moving in the distal and proximal directions within sleeve 30 and, therefore, securely and permanently locks holder 20 in the extended position.

FIG. 7 more clearly shows an example of the improved locking mechanism according to the present invention, and the interaction between segmented annular projection 36, ramps 25 and 27, and groove 26. The locking mechanism of the present invention is superior to those previously used in needle holder assemblies, since it includes a segmented annular projection 36 with each segment of projection 36 being free-standing, flexible and extending from wall 31 into the interior of sleeve 30 to mate with groove 26 on holder 20. As is shown in FIG. 7, if sleeve 30 is forced in the distal direction into holder 20, each flexible segment 36 is trapped by ramp 27 and expands within groove 26 to more securely retain holder 20 in the extended position. Therefore, sleeve 30 is prevented from moving in the distal direction since all the force in that direction is dissipated in the expansion of each flexible segment 36 in groove 26 on one side and wall 31 on the other side. Movement of holder 20 in the proximal direction is prevented because of the height of ramp 25 with respect to groove 26. The space between edge 42 of ramp 25 and the inner surface of wall 31 on sleeve 30 is too small to allow protrusion 36 do pass through. Therefore, holder 20 is also prevented from moving in the proximal direction by the locking mechanism. In addition, since wall 31 is solid and, therefore, does not deform or expand under the pressure from each segment 36, the locking mechanism provides a very secure locking action that is stronger than those that have been used in earlier needle holder assemblies.

Figure 8:
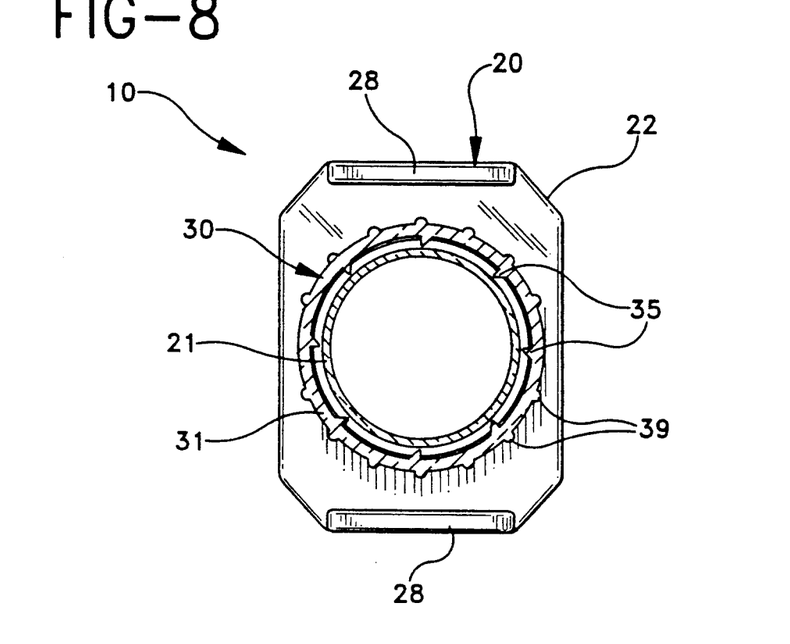
FIG. 8 is an end view of the needle holder assembly shown in FIGS. 1A and 2, showing the interaction of lead threads 35 and needle holder wall 21 when the assembly is in the retracted position.

FIG. 8 is an end view of needle holder assembly 10 shown in FIGS. 1A and 2, and more clearly shows the positioning of threads 35 and ribs 39. In addition, FIG. 8 shows the interaction between threads 35 and cylinder wall 21 on holder 20 from another perspective.

Figure 9:
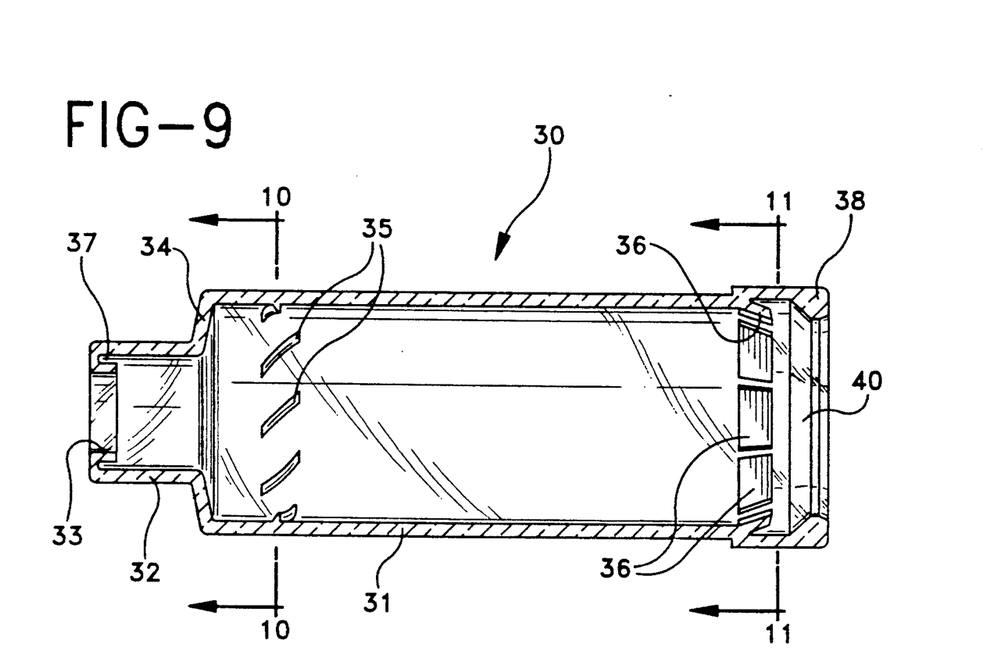
FIG. 9 is a cross-sectional view of sleeve 30 shown in assembly 10 in Figs. 1A and 1B.

FIG. 9 is a cross-sectional view of sleeve 30 before needle holder 20 has been inserted. As shown, shoulder 34 tapers to neck 32 at the distal end of sleeve 30 and segmented annular projection 36 and annular support 38 are positioned at the proximal end of sleeve 30. The positioning of the plurality of lead threads 35 on wall 31 inside sleeve 30 is also more clearly depicted in FIG. 9, and an annular channel 37 is shown surrounding the opening at the distal end of sleeve 30. Annular channel 37 prevents body fluid from splattering from the distal end of sleeve 30 when holder 20 has been used and locked in the extended position so that assembly 10 can be disposed of.

Figure 10:
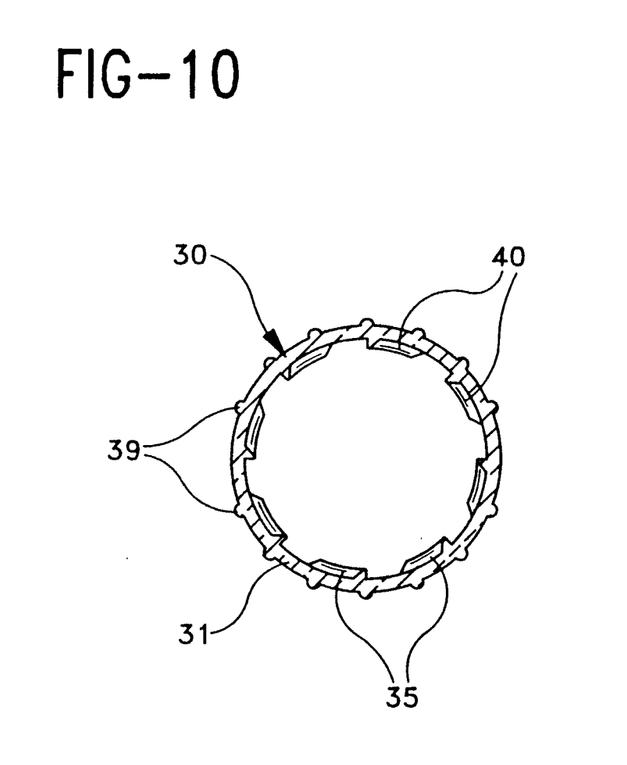
FIG. 10 is a cross-section taken along lines 10—10 of FIG. 9.
Figure 11:
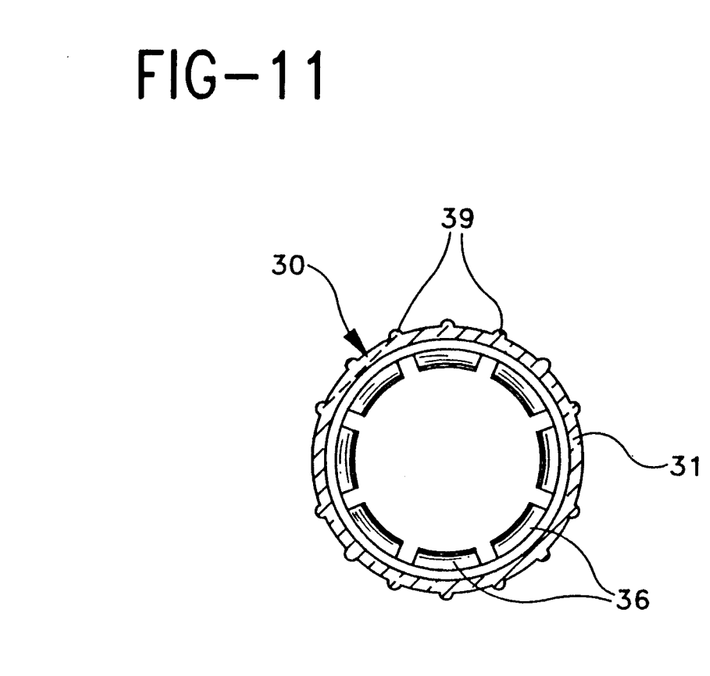
FIG. 11 is a cross-section taken along lines 11—11 of FIG. 9.

FIG. 10 is a cross-sectional view of sleeve 30 in FIG. 9, taken along lines 10—10, to show each beveled surface 40 on the plurality of lead threads 35 that provide the biting action needed between threads 35 and ramp 25, when rotating holder 20 to release it from the retracted position in sleeve 30. FIG. 11 is a cross-sectional view of sleeve 30 in FIG. 9, taken along lines 11—11, that more clearly shows the structure of segmented annular projections 36 and, more particularly, the spacing and shape of each free-standing flexible segment of annular projection 36.

A special loading device (not shown) is used to insert holder 20 into sleeve 30. The loading device is needed to ensure that each flexible segment of annular projection 36 lies flat against wall 31 when holder 20 is being inserted into sleeve 30 to permit it to slide to the retracted position in sleeve 30. As described above, after holder 20 is in the retracted position it can be easily and smoothly released from the retracted position by rotating holder 20 in a counterclockwise direction which slowly backs holder 20 out of the retracted position using the release mechanism of the present invention. After holder 20 is out of the retracted position, it can be freely slid to the extended position wherein it is securely and permanently locked in sleeve 30 by the locking mechanism discussed above.

Needle holder 20 and outer sleeve 30 are all made of molded plastic, however, of course, molded plastic is merely exemplary, various other materials could also be used.

In the foregoing discussion, it is to be understood that the above-described embodiments are simply illustrative of a disposable needle holder having a special releasing mechanism and locking mechanism according to the present invention. Other suitable variations and modifications could be made to the embodiment discussed above and still remain within the scope of the present invention.

What is claimed is:

1. A needle holder assembly comprising:
a sleeve having a main portion with an opening at a proximal end of said sleeve and a neck portion at a distal end of said sleeve that is connected to said main portion;
a needle holder slidably received within said sleeve through said opening for movement from a retracted position where a needle held in said needle holder extends through said neck portion of said sleeve, to an extended position where the needle is contained within said sleeve;

means for permanently locking said needle holder within said sleeve at said extended position, said locking means comprising:

a segmented annular projection having a plurality of flexible segments extending from an interior wall of said sleeve about said proximal end of said sleeve, each flexible segment being angled towards a distal end of said assembly to expand when under pressure; and a groove in a proximal end of said needle holder for receiving said plurality of flexible segments when said needle holder is in said extended position to permanently lock said needle holder and said sleeve together and prevent movement of said needle holder within said sleeve in both the proximal and distal directions because of the expansion of each angled flexible segment within said groove: and means for smoothly releasing said needle holder from said retracted position and permitting said needle holder to slide towards said extended position.

2. A needle holder assembly according to claim 1, wherein said means for releasing said needle holder from said retracted position is activated in response to rotation of said needle holder within said sleeve.

3. A needle holder assembly according to claim 1, wherein said means for releasing said needle holder from said retracted position includes a plurality of threads extending from an interior wall of said sleeve that mate with said needle holder, whereby said needle holder is released from said retracted position as said needle holder is rotated relative to said sleeve.

4. A needle holder assembly according to claim 1, wherein:

said sleeve further includes a shoulder connecting said main portion to said neck portion;

said needle holder further includes a shoulder at said distal end that contacts said sleeve shoulder when said needle holder is in said retracted position to prevent said needle holder from sliding in a distal direction within said sleeve; and said releasing means securely mates with said needle holder to prevent said needle holder from sliding in a proximal direction within said sleeve.

5. A needle holder assembly according to claim 1, further comprising means for supporting said needle holder within said sleeve about said proximal end.

6. A needle holder assembly according to claim 5, wherein said supporting means includes an annular support extending from said proximal end of said sleeve and contacting said needle holder.

7. A needle holder assembly according to claim 1, further comprising means for capturing liquid within said neck portion to prevent the liquid from splattering out of said sleeve.

8. A needle holder assembly according to claim 7, wherein said means for capturing liquid within said neck portion comprises an annular channel surrounding an opening at said distal end of said neck portion on said sleeve so to prevent the liquid from splattering out of said sleeve when said needle holder is locked in said extended position.

9. A needle holder assembly according to claim 8, wherein said channel has a shape of to half a hollow toroid.

10. A need holder assembly comprising:

a sleeve having a main portion with an opening at a proximal end of said sleeve and a neck portion at a distal end of said sleeve that is connected to said main portion;

a needle holder slidably received within said sleeve through said opening for movement from a retracted position where a needle held in said needle holder extends through said neck portion of said sleeve, to an extended position where the needle is contained within said sleeve; and means for permanently locking said needle holder within said sleeve at said extended position, said locking means comprising:

a segmented annular projection having a plurality of flexible segments extending from an interior wall of said sleeve about said proximal end of said sleeve, each flexible segment being angled towards a distal end of said assembly to expand when under pressure; and a groove in a proximal end of said needle holder for receiving said plurality Of flexible segments when said needle holder is in said extended position to permanently lock said needle holder and said sleeve together and prevent movement of said needle holder within said sleeve in both the proximal and distal directions because of the expansion of each angled flexible segment within said groove.

11. A needle holder assembly according to claim 10, wherein each of said segments is free-standing.

12. A needle holder assembly according to claim 10, wherein said needle holder further comprises:

a first ramp surrounding a distal end of said needle holder adjacent a distal end of said groove, said first ramp having an overall diameter that increases towards said groove; and a second ramp surrounding said needle holder adjacent a proximal end of said groove, said second ramp having an overall diameter that increases towards said groove, wherein said groove is located between said first ramp and said second ramp.

13. A needle holder assembly according to claim 12, wherein: each of said segments extend from said interior wall of said sleeve and are received between said first ramp and said second ramp in said groove; and said first ramp and said groove mate with each of said segments to prevent said needle holder from moving in both the proximal and distal directions.

14. A needle holder assembly according to claim 10, further comprising means for smoothly releasing said needle holder from said retracted position and permitting said needle holder to slide towards said extended position.

15. A needle holder assembly according to claim 14, wherein said means for releasing said needle holder from said retracted position includes a plurality of threads extending from said interior wall of said sleeve that mate with a surface on said needle holder, whereby said needle holder is released from said retracted position as said needle holder is rotated relative to said sleeve.

16. A needle holder assembly comprising:

a sleeve having a main portion with an opening at a proximal end of said sleeve and a neck portion at a distal end of said sleeve that is connected to said main portion;

a needle holder slidably received within said sleeve through said opening for movement from a retracted position where a needle held in said needle holder extends through said neck portion of said sleeve, to an extended position where the needle is contained within said sleeve;

means for smoothly releasing said needle holder from said retracted position and permitting said needle holder to slide towards said extended position;

means for permanently locking said needle holder within said sleeve at said extended position, said locking means comprising:

a segmented annular projection having a plurality of flexible segments extending from an interior wall of said sleeve about said proximal end of said sleeve, each flexible segment being angled towards a distal end of said assembly to expand when under pressure; and a groove in a proximal end of said needle holder for receiving said plurality of flexible segments when said needle holder is in said extended position to permanently lock said needle holder and said sleeve together and prevent movement of said needle holder within said sleeve in both the proximal and distal directions because of the expansion of each angled flexible segment within said groove; and means for capturing liquid within said neck portion to prevent the liquid from splattering out of said sleeve when said needle holder is not in said retracted position.

* * * * *